United States Patent
Liddicoat et al.

(10) Patent No.: US 6,913,608 B2
(45) Date of Patent: Jul. 5, 2005

(54) AUTOMATED ANNULAR PLICATION FOR MITRAL VALVE REPAIR

(75) Inventors: John R. Liddicoat, Sewickley, PA (US); Gregory H. Lambrecht, Natick, MA (US); Richard B. Streeter, Winchester, MA (US); Steven B. Woolfson, Boston, MA (US)

(73) Assignee: Viacor, Inc., Wilmington, MA (US)

( * ) Notice: Subject to any disclaimer, the term of this patent is extended or adjusted under 35 U.S.C. 154(b) by 320 days.

(21) Appl. No.: 10/004,474

(22) Filed: Oct. 23, 2001

(65) Prior Publication Data

US 2002/0095167 A1 Jul. 18, 2002

Related U.S. Application Data

(63) Continuation-in-part of application No. 09/888,282, filed on Jun. 22, 2001, now Pat. No. 6,702,826.
(60) Provisional application No. 60/242,466, filed on Oct. 23, 2000.

(51) Int. Cl.[7] .............................................. A61B 17/08
(52) U.S. Cl. .................... 606/151; 606/153; 606/219; 623/2.36
(58) Field of Search ................................ 606/139, 151, 606/75, 219, 220, 221, 232, 157, 158; 623/2.36, 2.37, 2.4; 128/898; 227/175.1

(56) References Cited

U.S. PATENT DOCUMENTS

| | | | |
|---|---|---|---|
| 4,505,273 A | 3/1985 | Braun et al. | |
| 4,841,960 A | 6/1989 | Garner | |
| 5,236,440 A | 8/1993 | Hlavacek | |
| 5,450,860 A | 9/1995 | O'Connor | |
| 5,540,716 A | 7/1996 | Hlavacek | |
| 5,709,695 A | 1/1998 | Northrup, III | |
| 5,716,370 A * | 2/1998 | Williamson et al. | 606/153 |
| 5,947,999 A | 9/1999 | Groiso | |
| 5,993,476 A | 11/1999 | Groiso | |
| 6,203,553 B1 * | 3/2001 | Robertson et al. | 606/139 |
| 6,482,224 B1 * | 11/2002 | Michler et al. | 606/219 |
| 2003/0120340 A1 | 6/2003 | Liska et al. | |
| 2003/0171776 A1 | 9/2003 | Adams et al. | |

* cited by examiner

*Primary Examiner*—Julian W. Woo
(74) *Attorney, Agent, or Firm*—Pandiscio & Pandiscio (57) ABSTRACT

A novel system for performing a heart valve annuloplasty. The system involves the use of a plication band. In one embodiment, the annulus of the valve is reduced by constriction of the plication band itself. More particularly, each plication band enters the tissue at two or more points which are spaced from one other by a distance which is dictated by the geometry of the plication band. Subsequent constriction of the plication band causes these points to move toward each other, thereby constricting the tissue trapped between these points and thus reducing the overall circumference of the valve annulus. In a second embodiment, the annulus of the valve is reduced by linking multiple plication bands to one other, using a linkage construct, and then using a shortening of the length of the linkage construct between each plication band so as to gather the tissue between each plication band, whereby to reduce the overall circumference of the valve annulus.

2 Claims, 12 Drawing Sheets

AUTOMATED ANNULAR PLICATION FOR MITRAL VALVE REPAIR

REFERENCE TO PENDING PRIOR PATENT APPLICATION

This is a continuation-in-part of prior U.S. patent application Ser. No. 09/888,282, filed Jun. 22, 2001, now U.S. Pat. No. 6,702,826 by John R. Liddicoat et al. for AUTOMATED ANNULAR PLICATION FOR MITRAL VALVE REPAIR.

This patent application also claims benefit of pending prior U.S. Provisional Patent Application Ser. No. 60/242,466, filed Oct. 23, 2000 by Richard B. Streeter for MYOBAND.

The aforementioned two patent applications are hereby incorporated herein by reference.

BACKGROUND OF THE INVENTION

Mitral valve repair is the procedure of choice to correct mitral regurgitation of all etiologies. With the use of current surgical techniques, between approximately 70% and 95% of regurgitant mitral valves can be repaired. The advantages of mitral valve repair over mitral valve replacement are well-documented. These include better preservation of cardiac function and reduced risk of anticoagulant-related hemorrhage, thromboembolism and endocarditis.

Nearly all mitral valve repairs include an annuloplasty. The annuloplasty consists of a suture or prosthetic ring that surrounds all or part of the circumference of the annulus of the mitral valve. The annuloplasty serves several functions: it remodels the annulus of the valve; it decreases tension on suture lines; it increases leaflet coaptation; and it prevents recurrent annular dilatation. In addition, the annuloplasty improves repair durability.

Most current annuloplasty techniques require the placement of sutures in the mitral annulus followed by placement of a prosthetic band or ring. This technique can be time-consuming and technically difficult. Furthermore, using current techniques, the annuloplasty requires cardiopulmonary bypass, cardiac arrest, and a large incision in the chest wall and heart.

It is well-known that cardiopulmonary bypass is associated with significant morbidity and mortality. Recognition of the damaging effects of cardiopulmonary bypass has been the impetus for significant advances in beating heart coronary artery bypass grafting. As a consequence, approximately 20% to 35% of all coronary artery bypass grafting is now performed on a beating heart. To date, however, there are no clinically-applicable techniques for performing mitral valve surgery on a beating heart without the use of a heart-lung machine. Therefore, mitral valve repair by annuloplasty currently entails a major operation that includes all of the complications attributable to cardiopulmonary bypass.

In current practice, all patients judged to be candidates for mitral valve surgery must face the risk of cardiopulmonary bypass and cardiac arrest. Therefore, patients early in their disease process (i.e., those who have not yet suffered significant cardiac damage) generally have surgery deferred until they develop troubling symptoms or cardiac dysfunction. Conversely, other patients (i.e., those with poor cardiac function and other co-morbidities) are frequently denied surgery as the risk associated with cardiopulmonary bypass and cardiac arrest is too high.

Mitral regurgitation is common in patients with poor cardiac function and heart failure. It is well known that mitral regurgitation contributes significantly to the debilitating symptoms of such patients. Correction of mitral regurgitation would improve symptoms and, possibly, longevity in such patients. Furthermore, it is believed that mitral regurgitation contributes to the deterioration of left ventricular function. Thus, correcting mitral regurgitation may halt further decline in ventricular function and may, in fact, cause improvement in ventricular function.

Unfortunately, however, such heart failure patients are at high risk for mitral valve surgery using current techniques. By way of example, the operative mortality for mitral valve surgery in patients with left ventricular dysfunction is approximately 5% to 15%. Therefore, the majority of such patients are not deemed candidates for mitral valve repair using currently available techniques.

Development of a system and method for mitral valve annuloplasty that does not require cardiopulmonary bypass would extend the benefits of mitral valve repair to a large segment of the heart failure population.

SUMMARY OF THE INVENTION

Accordingly, one object of the present invention is to provide an improved system for the repair of heart valves.

Another object of the present invention is to provide an improved system for the repair of heart valves so as to improve their efficiency.

And another object of the present invention is to provide an improved system for the repair of mitral valves.

Still another object of the present invention is to provide an improved system to reduce mitral regurgitation.

Yet another object of the present invention is to provide an improved system for mitral valve annulopasty.

Another object of the present invention is to provide an improved system for the repair of mitral valves that can be used with other repair techniques that might involve leaflets, chordae tending and/or papillary muscles.

Another object of the present invention is to provide a novel system that may stabilize or improve left ventricular function.

Another object of the present invention is to provide a novel system that may treat congestive heart failure.

Another object of the present invention is to provide a novel system that may prevent the development o f mitral regurgitation, prospectively.

And another object of the present invention is to provide a novel system for the repair of mitral valves that eliminates the need for cardiopulmonary bypass and/or cardiac arrest.

Still another object of the present invention is to provide a novel system for the repair of mitral valves that facilitates the use of smaller incisions.

Yet another object of the present invention is to provide a novel system for the repair of mitral valves that affords a percutaneous approach to the mitral valve.

Another object of the present invention is to provide a novel system for the repair of mitral valves, wherein the system can be employed to perform mitral valve repair via a partial or complete annuloplasty, either on an arrested heart or on a beating heart, with or without the use of cardiopulmonary bypass, or on a fibrillating heart.

Another object of the present invention is to provide an improved method for the repair of heart valves.

Another object of the present invention is to provide an improved method for the repair of heart valves so as to improve their efficiency.

And another object of the present invention is to provide an improved method for the repair of mitral valves.

Still another object of the present invention is to provide an improved method to reduce mitral regurgitation.

Yet another object of the present invention is to provide an improved method for mitral valve annulopasty.

Another object of the present invention is to provide an improved method for the repair of mitral valves that can be used with other repair techniques that might involve leaflets, chordae tending and/or papillary muscles.

Another objective of the present invention is to provide a novel method that may stabilize or improve left ventricular function.

Another object of the present invention is to provide a novel method that may treat congestive heart failure.

Another object of the present invention is to provide a method that may prevent the development of mitral regurgitation, prospectively.

And another object of the present invention is to provide a novel method for the repair of mitral valves that eliminates the need for cardiopulmonary bypass and/or cardiac arrest.

Still another object of the present invention is to provide a novel method for the repair of mitral valves that facilitates the use of smaller incisions.

Yet another object of the present invention is to provide a novel method for the repair of mitral valves that affords a percutaneous approach to the mitral valve.

Another object of the present invention is to provide a novel method for the repair of mitral valves, wherein the method can be employed to perform mitral valve repair via a partial or complete annuloplasty, either on an arrested heart or on a beating heart, with or without the use of cardiopulmonary bypass, or on a fibrillating heart.

These and other objects of the present invention are addressed by the provision and use of a novel system and method for performing partial or complete mitral valve annuloplasty using a novel device that creates a measured plication of the mitral annulus. The device can be inserted into the left atrium via (1) a partial or complete sternotomy; (2) a right or left thoracotomy, with or without a thorocoscope; or (3) a central or peripheral vein via the right atrium and interatrial septum.

Alternatively, the device may be applied to the outside of the heart, via any incision, such that the device effects a geometrical change in the annulus. Alternatively, the device can be inserted into any cardiac vein or artery in the heart such that the device causes a geometric change in the mitral annulus.

Further, the device may be applied to the outside of the heart in association with another device such as a restraining device used for the treatment of heart failure. In so doing, the device may be responsible for altering the mitral valve and/or left ventricle in such a way as to influence mitral regurgitation, heart function, and/or congestive heart failure.

Visualization of the device within the left atrium can be facilitated by transesophageal echocardiography; epicardial echocardiography; fluoroscopy; angioscopy; an ultrasound probe that is or is not an integral part of the device; or an angioscope that is or is not an integral part of the device.

The device is adapted to deploy plication bands into the mitral annulus. Each plication band comprises two ends which penetrate the tissue of the mitral annulus, thereby affixing the plication band to the annular tissue. Preferably each plication band engages about 5–15 mm of annular tissue. As the plication band is deployed, it plicates the annular tissue immediately below the plication band by about 30% to 50%, thereby reducing the annular circumference of the mitral annulus in measured increments. The distal end of the device, which has a range of motion controlled by the operator, may then be rotated 180 degrees, thus maintaining a point of engagement with the mitral annulus (or, if desired, the left atrium). Alternatively, the device may be detached completely from the annulus before deployment of the next plication band. The aforementioned rotation of the device can be helpful since it can aid in the measured placement of the next plication band. However, there may be occasions in which the operator may not want the device to rotate. In that situation, the same or similar device may be used without rotation.

The plication bands may be separate from one another, or they may be attached to one another via a linkage construct. Where a plurality of plication bands are attached to one another via a linkage construct, the valve annulus may also be reduced by a shortening of the length of the linkage construct between each plication band so as to gather together the tissue between each plication band.

Each plication band may be constructed of a substantially rigid or semi-flexible metal or other material. The plication band is adapted to be non-thrombogenic and may be coated, in whole or in part, by a material designed to promote tissue in-growth and reduce thromboembolism. By way of example but not limitation, such material might be dacron, polyester velour, pericardium, or some other suitable material.

The device may be used on a fully arrested heart with the patient on cardiopulmonary bypass, or on a beating heart with or without cardiopulmonary bypass, or on a fibrillating heart. If employed on a beating heart or on a fibrillating heart, the device may be introduced into the left atrium via the left atrium wall, a pulmonary vein, the left atrial appendage, or percutaneously into the left atrium via a systemic vein. The device may also be introduced into the left atrium via the arterial system and across the aortic valve. If employed during cardiopulmonary bypass, the device may be introduced into the left atrium in a similar fashion, with or without robotic assistance.

It should be appreciated that while the device is generally discussed herein with reference to its use in mitral valve repair, it is also contemplated that the same or substantially similar device and methodology may be used in the repair of other cardiac valves, including the tricuspid valve, the pulmonary valve, and the aortic valve.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like elements and further wherein.

DETAILED DESCRIPTION OF THE PREFERRED EMBODIMENTS

The plication bands of the present invention allow plication of a valve annulus using one or both of two methods.

The first method of reducing the valve annulus is by constriction of the plication band itself. Each plication band enters the annulus tissue at two or more points which are spaced from one other by a set distance which is dictated by the geometry of the plication band. Subsequent constriction of the plication band causes these points to move toward each other, thereby constricting the tissue trapped between these points and thus reducing the overall circumference of the valve annulus.

The second method of reducing the valve annulus is by linking multiple plication bands to one other, using a linkage construct, and then using a shortening of the length of the linkage construct between each plication band so as to gather the tissue between each plication band, whereby to reduce the overall circumference of the valve annulus.

Figures 1, 2:
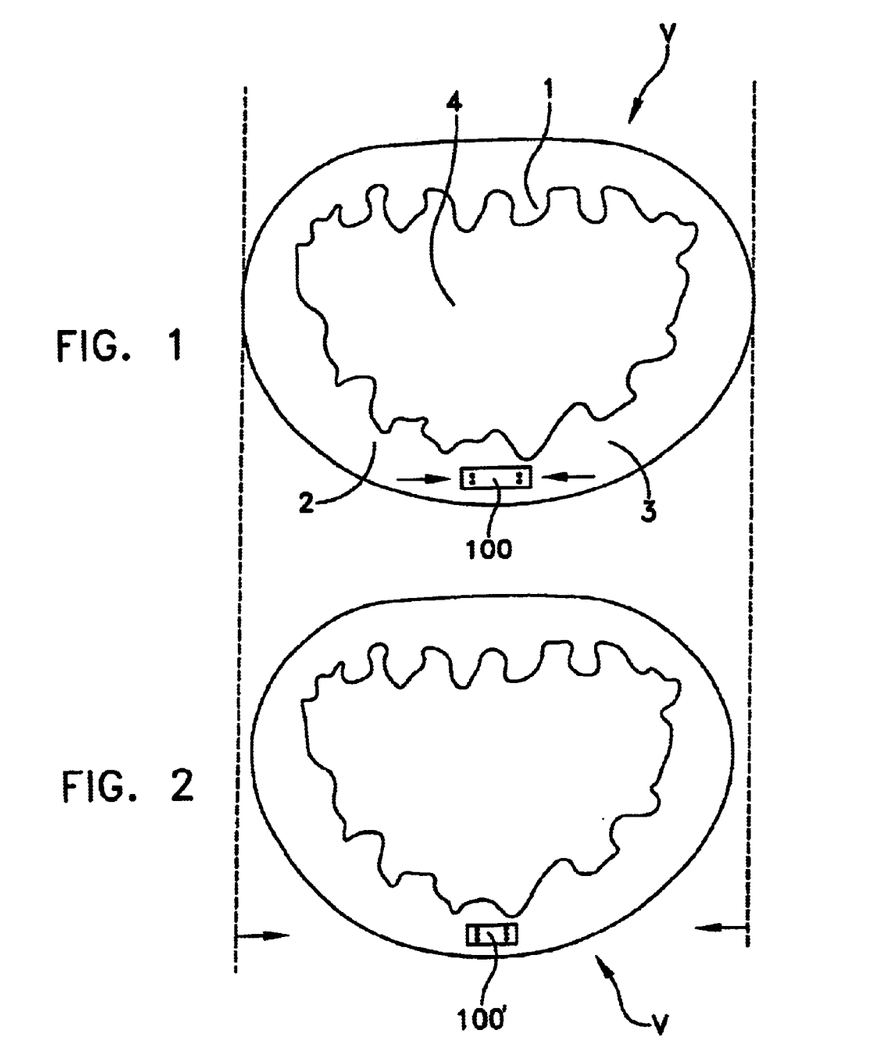
FIG. 1 is a schematic diagram showing the placement of a single plication band into the dilated annulus of a cardiac valve, with the plication band being shown in its open, un-constricted state, with both ends of the plication band piercing the tissue of the annulus.
FIG. 2 is a schematic diagram similar to that of FIG. 1, except showing the plication band following constriction of the plication band, and with the circumference of the annulus having been reduced by the amount of constriction undergone by the plication band.
Figure 7:
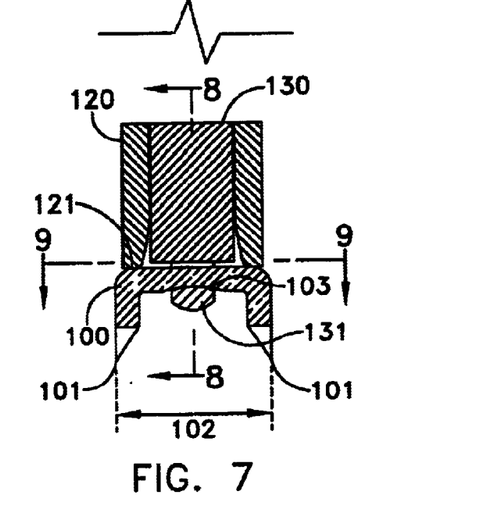
FIG. 7 is a schematic front sectional view of an exemplary plication band and deployment tool of the present invention, with the plication band and deployment tool being shown prior to deployment of the plication band into tissue.
Figure 8:
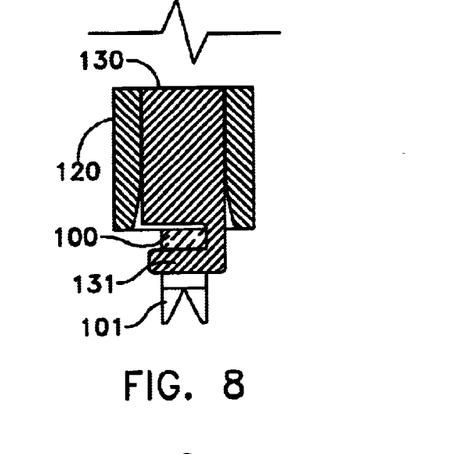
FIG. 8 is schematic side sectional view taken along line 8—8 of FIG. 7.
Figure 9:
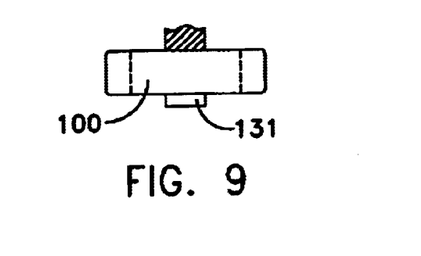
FIG. 9 is a schematic top sectional view taken along line 9—9 of FIG. 7.
Figure 10:
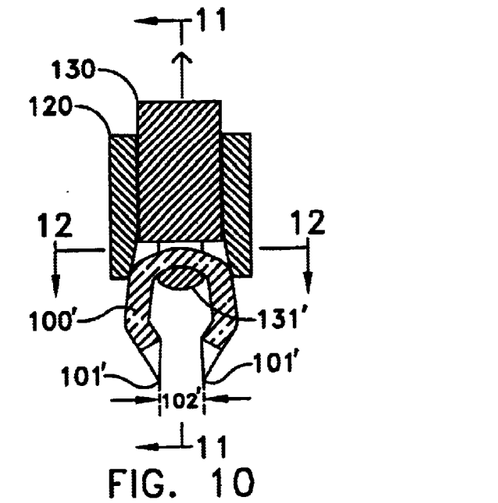
FIG. 10 is a schematic front sectional view of the plication band and deployment tool of FIG. 7, except shown after deployment of the plication band into tissue (not shown)
Figure 11:
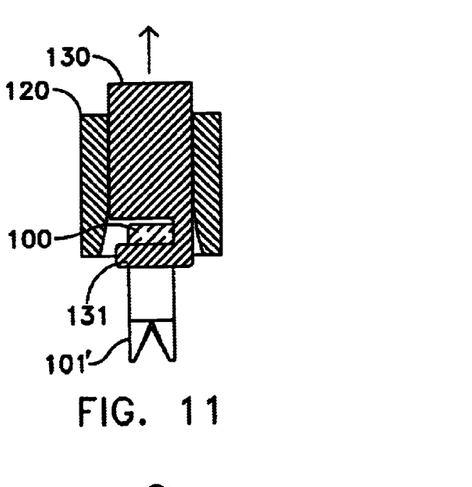
FIG. 11 is a schematic side sectional view taken along line 11—11 of FIG. 10.
Figure 12:
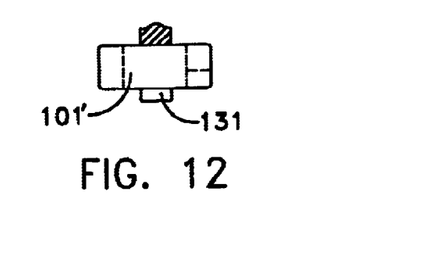
FIG. 12 is a schematic top sectional view taken along line 12—12 of FIG. 10.

In one exemplary embodiment, the plication band initially has the form of the un-constricted staple 100 shown in FIGS. 7–9, with two sharpened ends 101 separated by a distance 102. These two sharpened ends 101 are suitable for piercing the annulus tissue 3 of a valve V shown in FIG. 1 Upon deformation of the plication band 100 into a constricted state 100', as depicted in FIGS. 10–12, the distance between sharpened ends 101 reduces to the distance 102'. This reduction in distance constricts the annulus tissue located between ends 101, thereby causing a corresponding reduction in the circumference of the annulus 3 of the valve V, such as shown in FIG. 2. As a result, mitral regurgitation in valve V will be reduced.

As will hereinafter be discussed, the plication band is not limited to the particular geometry of the plication band 100 shown in FIGS. 7–12. Many different plication band designs will be consistent with the scope of the present invention.

Thus, for example, the plication band may be configured to pierce the valve tissue at more than two locations if desired; or the plication band may be designed to pierce only a portion of the annulus 3, leaving another part of the plication band embedded in other tissue; or the sharpened ends of the plication band may employ reverse barbs that help resist the inadvertent withdrawal of the sharpened ends from heart tissue; etc.

The final deformed shape 100', and the difference between the un-deformed distance 102 and the deformed distance 102', can be varied, either by plication band design or by the design of the deployment tool which deforms the plication band. For mitral annuloplasty, the distance 102 is preferably between about 3 mm and 20 mm, with the distance 102' being about 20% to 70% of distance 102. However, these distances may vary outside of these ranges, particularly where the present invention is applied to other cardiac valves.

Plication band 100 may be formed from many suitable materials including, but not limited to, biocompatible metals such as 3-series stainless steels, titanium alloys, and resorbable and non-resorbable polymers. The plication bands may additionally be coated with thin layers of non-thombogenic materials or tissue in-growth matrices.

Figure 3:
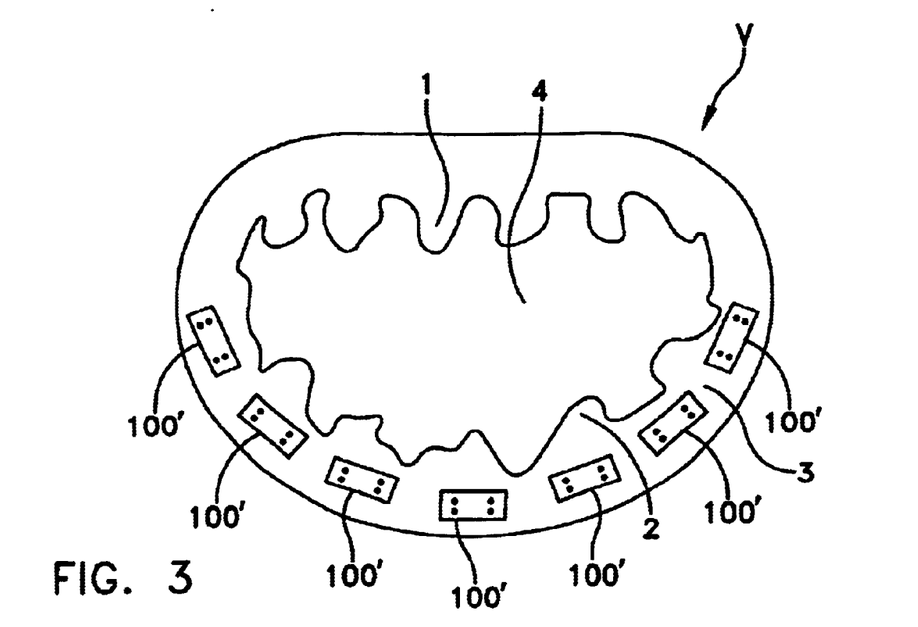
FIG. 3 is a schematic diagram showing the placement of a plurality of plication bands into the annulus of a cardiac valve, with the plication bands being shown after constriction of the bands, whereby to effect the desired aggregate reduction in the circumference of the valve annulus.

Multiple plication bands 100 may be employed to generate a greater reduction in a valve annulus. As shown in FIG. 3, a plurality of plication bands 100' may be deployed, independently of one another, about the annulus of the valve. In this situation, the number of plication bands 100' placed into annulus 3 determines the overall reduction in the circumference of the annulus. It should be appreciated that the valve shown in FIG. 3 (and FIGS. 1, 2 and 4–6 as well) is the mitral valve as viewed from the left atrium. Posterior leaflet 2 and anterior leaflet 1 coapt to close valve orifice 4 during systole. Plication bands 100' act in concert with one another so as to create the desired annular reduction by the sum of their individual constrictions.

Figure 4:
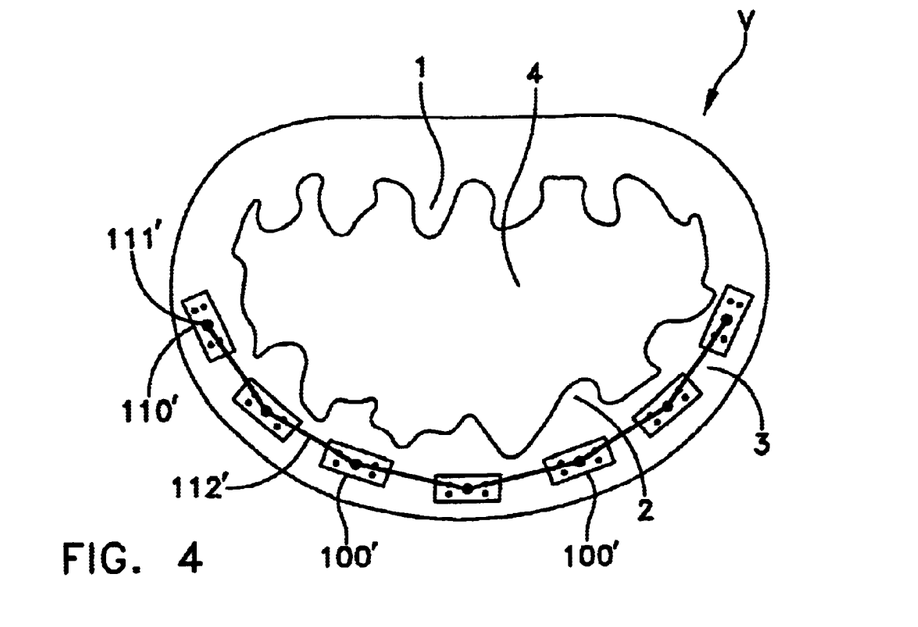
FIG. 4 is a schematic diagram similar to that of FIG. 3, except that the plication bands are linked to one another by a series of linear linkages, such that the linear linkages may also help to effect the desired reduction in the circumference of the valve annulus.
Figure 5:
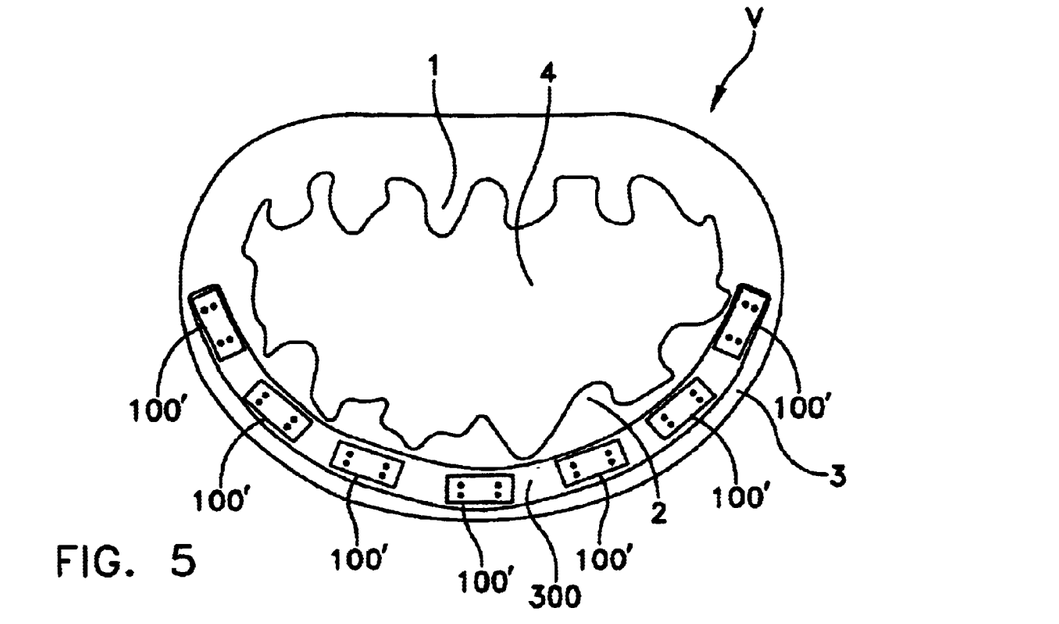
FIG. 5 is a schematic diagram similar to that of FIG. 3, except that the plication bands are linked to one another by a linkage strip, such that the linkage strip may also help to effect the desired reduction in the circumference of the valve annulus.
Figure 6:
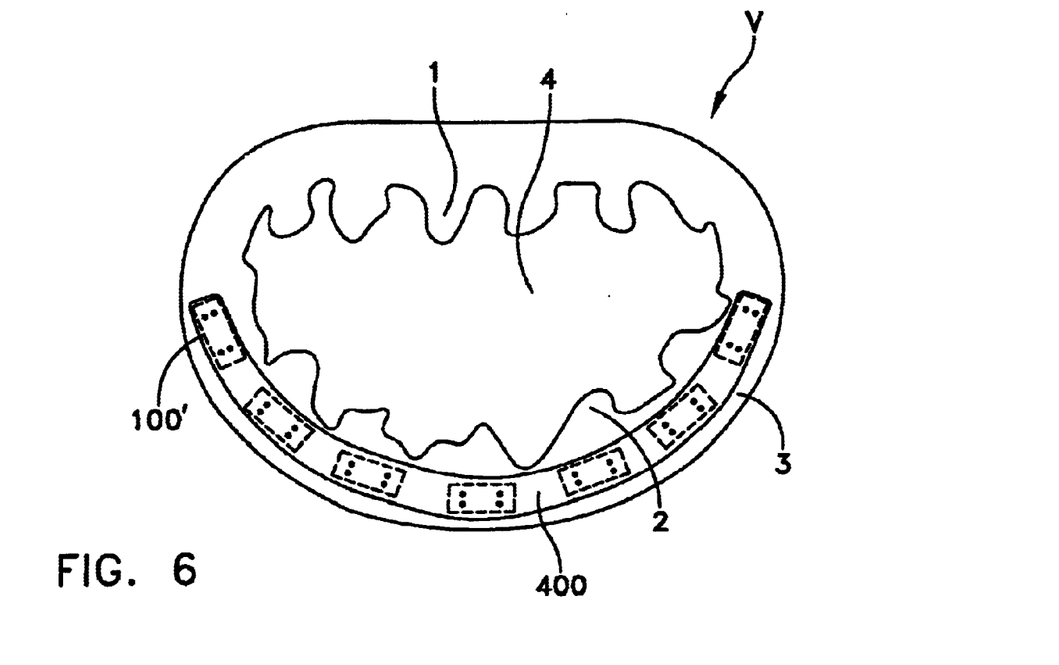
FIG. 6 is a schematic diagram similar to that of FIG. 3, except that the plication bands are linked to one another by a linkage rod, such that the linkage rod may also help to effect the desired reduction in the circumference of the valve annulus.

Alternatively, as shown in FIGS. 4–6, the individual plication bands 100 may be linked to one another by a linkage construct that restricts the distance between, and in some cases the relative rotational and angular orientation of, at least some of the plication bands 100.

Some or all of the plication bands may be linked by a plurality of linear linkages such as is shown in FIG. 4. Here, seven plication bands 1101 are linked to one another by six linear linkages 112'. Each linear linkage 112' links one plication band 100 to a neighboring plication band 100 and is secured at points 111'. These linear linkages attach neighboring plication bands to one another. The linear linkages themselves may be used to further reduce the circumference of the valve annulus.

More particularly, where the linear linkages are formed out of an elastic material, after deformation of a first band 100', tension may be applied to the linear linkage 112' which connects that first plication band 100' to a neighboring second plication band 100. Then the second plication band 100 may be inserted into the valve tissue so that the tension in linear linkage 112' thereafter causes a constriction of the valve annulus between the first and second plication bands, thus decreasing the circumference of the annulus beyond that generated solely by deformation of the individual plication bands.

Alternatively, where the linear linkages are formed out of a formable material which will take a set, the plication bands may be set into the tissue of the annulus and then one or more of the linear linkages deformed so as to draw neighboring plication bands closer together, whereby to further reduce the circumference of the valve annulus.

Figure 14:
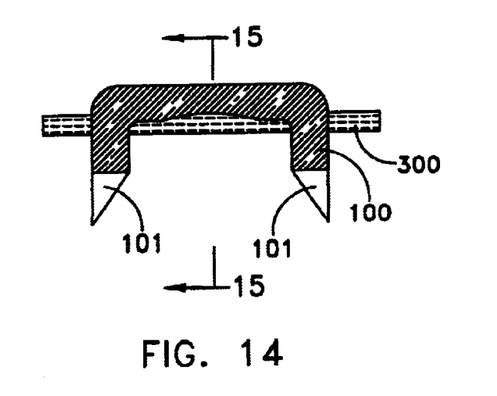
FIG. 14 is a front schematic sectional view showing a plication band coupled to a linkage strip.
Figure 15:
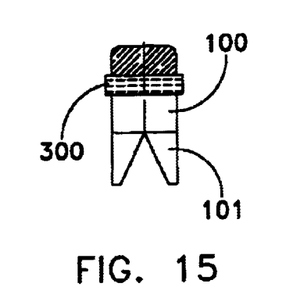
FIG. 15 is a side sectional view taken along line 15—15 of FIG. 14.
Figure 16:
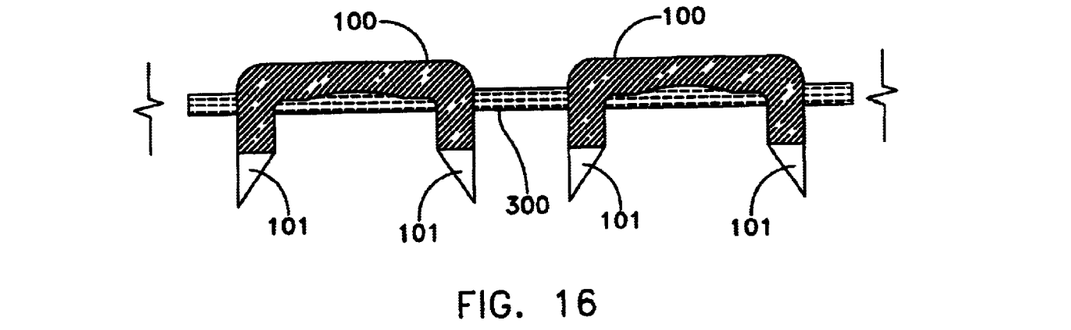
FIG. 16 is a schematic view similar to that of FIG. 14, except showing a plurality of plication bands coupled to, and linked by, a linkage strip.

FIG. 5 shows an alternative embodiment of the plication bands-and-linkage construct. More particularly, with this embodiment, plication bands 100' are linked by a linkage strip 300. The sharpened ends 101 of plication bands 100 pierce linkage strip 300 as shown in FIGS. 14–16. The sharpened ends of plication bands 100 may then be inserted into the tissue of annulus 3 and each plication band 100 deformed into its final shape 100', sandwiching linkage strip 300 between plication band 100' and valve annulus 3. Again, the linkage strip itself can be used to further reduce the circumference of the valve annulus.

More particularly, where linkage strip 300 is formed out of an elastic material, tension may be applied to the linkage strip between successive plication band deployments, whereby to cause a decrease in the circumference of the valve annulus.

Alternatively, where linkage strip 300 is formed out of a formable material which will take a set, the plication bands may be set into the tissue of the annulus and then the linkage strip deformed at one or more locations so as to draw neighboring plication bands closer together, whereby to further reduce the circumference of the valve annulus.

Linkage strip 300 may be formed from a variety of suitable materials including, but not limited to, woven, un-woven or expanded polymers, felts, and resorbable polymers such as polyglycolic acid (PGA), collagen, or the like.

Figure 17:
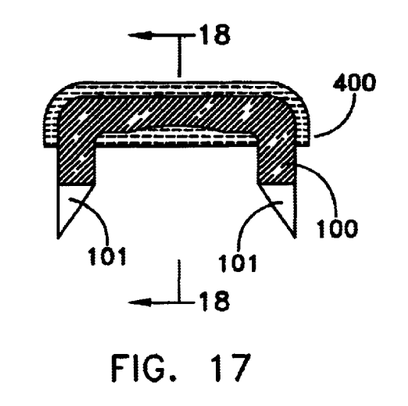
FIG. 17 is a schematic front sectional view showing a plication band coupled to a linkage rod.
Figure 18:
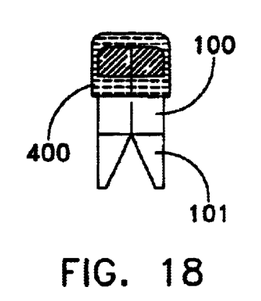
FIG. 18 is a side sectional view taken along line 18—18 of FIG. 17.
Figure 19:
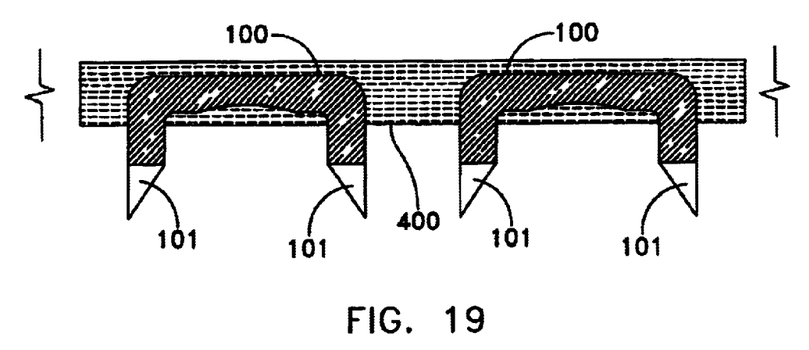
FIG. 19 is a schematic view similar to that of FIG. 17, except showing a plurality of plication bands coupled to, and linked by, a linkage rod.

Plication bands 100 may alternatively be imbedded in a linkage rod 400 such as is shown in FIGS. 6 and 17–19. The sharpened ends 101 of plication bands 100 preferably protrude outside of linkage rod 400 as shown in FIGS. 17–19 so as to allow sharpened ends 101 to easily penetrate the tissue of annulus 3. Again, the linkage rod itself can be used during implantation of the plication bands to further reduce the circumferences of the valve annulus.

More particularly, where linkage rod 400 is formed out of an elastic material, tension may be applied to the linkage rod between successive plication band deployments, whereby to cause a decrease in the circumference of the valve annulus.

Alternatively, where linkage rod 400 is formed out of a formable material which will take a set, the plication bands may be set into the tissue of the annulus and then the linkage rod deformed at one or more locations so as to draw neighboring plication bands closer together, whereby to further reduce the circumference of the valve annulus.

Alternatively, plication bands 100 may be made independent of one another but still include a portion of the linkage strip 300 (FIGS. 14 and 15) or a portion of the linkage rod 400 (FIGS. 17 and 18). The linkage strip 300 of FIGS. 14 and 15 acts as a pledget and may encourage in-growth into the implant. The linkage rod 400 of FIGS. 17 and 18 covers plication band 100 and may be used to reduce the thrombogenicity of the implant and/or encourage tissue in-growth.

All or some of the plication bands may be rigidly, flexibly, or movably secured to the linking construct (i.e., linear linkages 112', linkage strip 300 and/or linkage rod 400).

Rigid fixation is advantageous in providing a fixed distance between the plication bands and/or a fixed angular orientation to the bands. This can be accomplished through the use of a rigid linkage material and a rigid attachment of that material to the plication bands.

Flexible fixation can be employed to allow a variable distance between the plication bands and/or a variable angular orientation to the plication bands. Such flexible fixation may be accomplished by rigidly securing a flexible and/or elastic linkage material or construct to the plication band. Suitable flexible linkage constructs include, but are not limited to, woven or un-woven lengths of polymeric suture, strips or rods of woven or un-woven metals or polymers, filaments of elastic metals such as nickel titanium alloys, or small coil springs constructed of any suitable elastic material. Flexible fixation may also be accomplished by employing a pivoting or flexible attachment mechanism for securing a rigid linkage material or construct to the plication band. An exemplary embodiment of this system includes a linkage construct formed by a relatively rigid rod that passes through holes formed in each plication band. Such a construct might also allow the plication bands to slide along, and/or revolve about, the relatively rigid rod.

Figure 22:
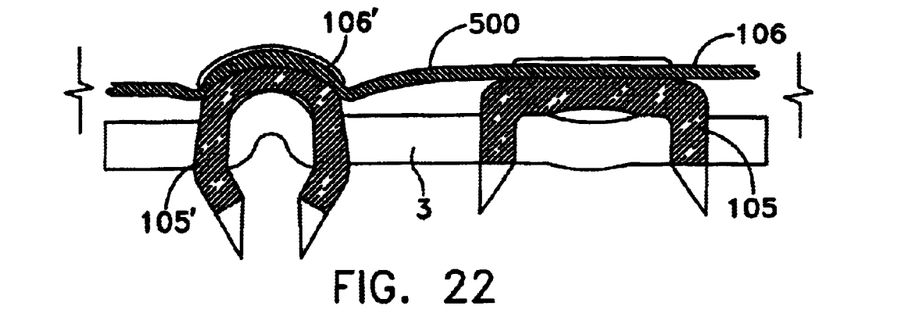
FIGS. 22–24 are front schematic views, partially in section, showing a method of applying linked plication bands of the sort shown in FIGS. 20 and 21 to the annulus of a heart valve so as to effect the desired reduction in the circumference of the valve annulus.
Figure 23:
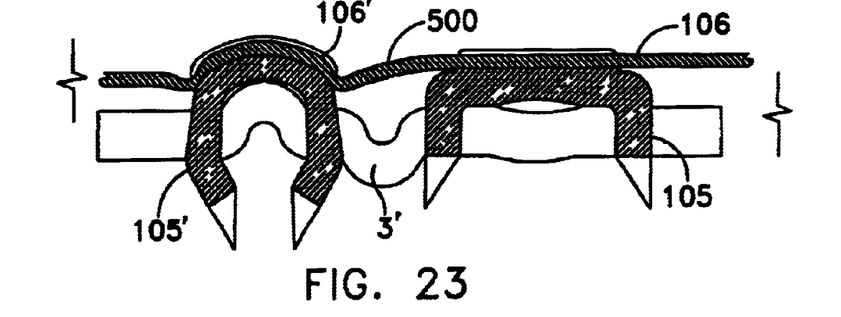
Figure 24:
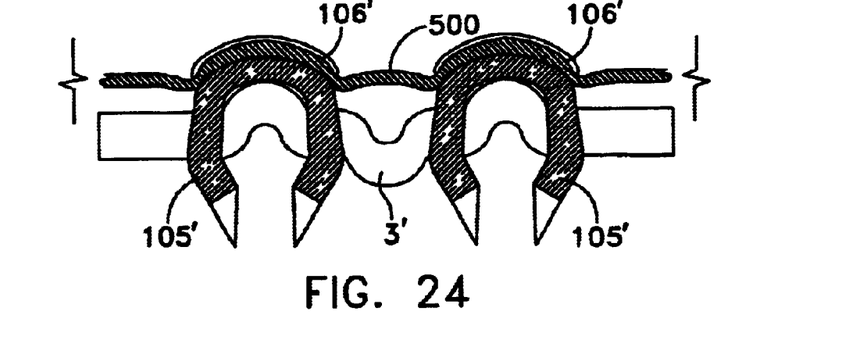

In a preferred embodiment, a flexible linkage such as a length of filament links each plication band to its neighbor. As shown in FIGS. 22–24, filament 500 can pass through through-holes 106 formed in each plication band 105. Plication bands 105 may slide along the length of filament 500. In a preferred application of this embodiment, filament 500 may first slide freely through through-hole 106 and then be rigidly secured to plication band 105 during, or after, contraction of band 105 into its deformed shape 105' within the annular tissue. Filament 500 may be rigidly secured to band 105' by collapsing through-hole 106 to a smaller orifice 106', thereby causing the material surrounding through-hole 106' to pinch filament 500 and prevent movement through through-hole 106'. Through-hole 106 may be collapsed during the contraction of plication band 105 by a plication band deployment device similar to that depicted in FIGS. 7, 8, 10 and 11. This may be accomplished by the deployment device crushing the metal about the through-hole 106 during bending of the plication band in the manner shown in FIGS. 10 and 11. Alternatively, a separate device or a separate component of the plication band deployment device may be employed to crush the through-hole independent of the contraction of the plication band.

There are also many other ways of rigidly securing filament 500 to plication band 105 that do not involve the crushing of a through-hole passing through plication band 105. A loop of suture attached to plication band 105 may be used to form a through-hole and then may be pulled tight against filament 500 so as to restrict movement of the filament relative to plication band 105. Still other configurations will be apparent to those skilled in the art in view of the present disclosure.

Figure 20:
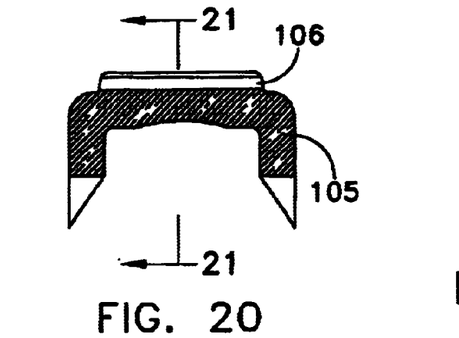
FIG. 20 is a schematic front sectional view of a plication band which may be attached to adjacent plication bands by a linkage filament.
Figure 21:
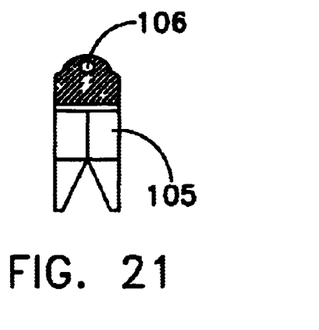
FIG. 21 is a sectional view taken along line 21—21 of FIG. 20.

In a preferred method of using the embodiment of FIGS. 20 and 21 to affect a desired reduction in the circumference of a valve annulus, tension is applied to filament 500 prior to rigidly securing filament 500 to plication band 105. As shown in FIGS. 22 and 23, this tension causes neighboring anchored plication bands to move toward the unanchored plication band along filament 500. This motion creates a greater reduction in valve annulus 3 than where the plication bands are applied individually. Once the second plication band is deformed and through-hole 106 is constricted to its reduced orifice 106', the neighboring plication bands 105' cannot move along filament 500, thus leaving the annulus tissue between plication bands 105' in constricted state 3'.

FIGS. 7–12 depict a method of actively contracting a plication band, by plastically deforming the plication band, into a final desired shape. Hook 131 of central pull rod 130 contacts the lower surface of the central region 103 of plication band 100. Outer pusher cannula 120 rests against the upper surface of plication band 100 on either side 121 of central region 103. By retracting central pull rod 130 relative to outer pusher cannula 120, plication band 100 can be plastically deformed about central region 103 into the deformed shape 100', thereby decreasing the distance 102 between ends 101 to the shorter distance 102' and curving the plication band 100 into a loop that resists inadvertent withdrawal from the tissue of the annulus. If desired, the deformed plication band 100' may be released from the tissue of the annulus by advancing central pull rod 130 relative to outer pusher cannula 120 and then disengaging hook 131 from the central region 103 of plication band 100.

Alternatively, the plication band of the present invention may be constructed of an elastic material such as a superelastic nickel titanium alloy (e.g., Nitinol) pre-formed in the desired final "contracted" shape. This shape can be the same as or similar to that shown in FIGS. 10–12. The plication band may then be deployed by actively expanding it, with an appropriate deployment tool, to a shape the same as or similar to that shown in FIGS. 7–9. The expanded plication band may then be advanced into annulus tissue and release; once released, the plication band will then elastically strain back into its original "contracted" shape.

The devices of the present invention may be applied through a variety of surgical and non-surgical approaches. They may be inserted with or without cardiopulmonary bypass, and from a variety of access sites, into the vascular system and/or cardiac chambers.

Figure 13:
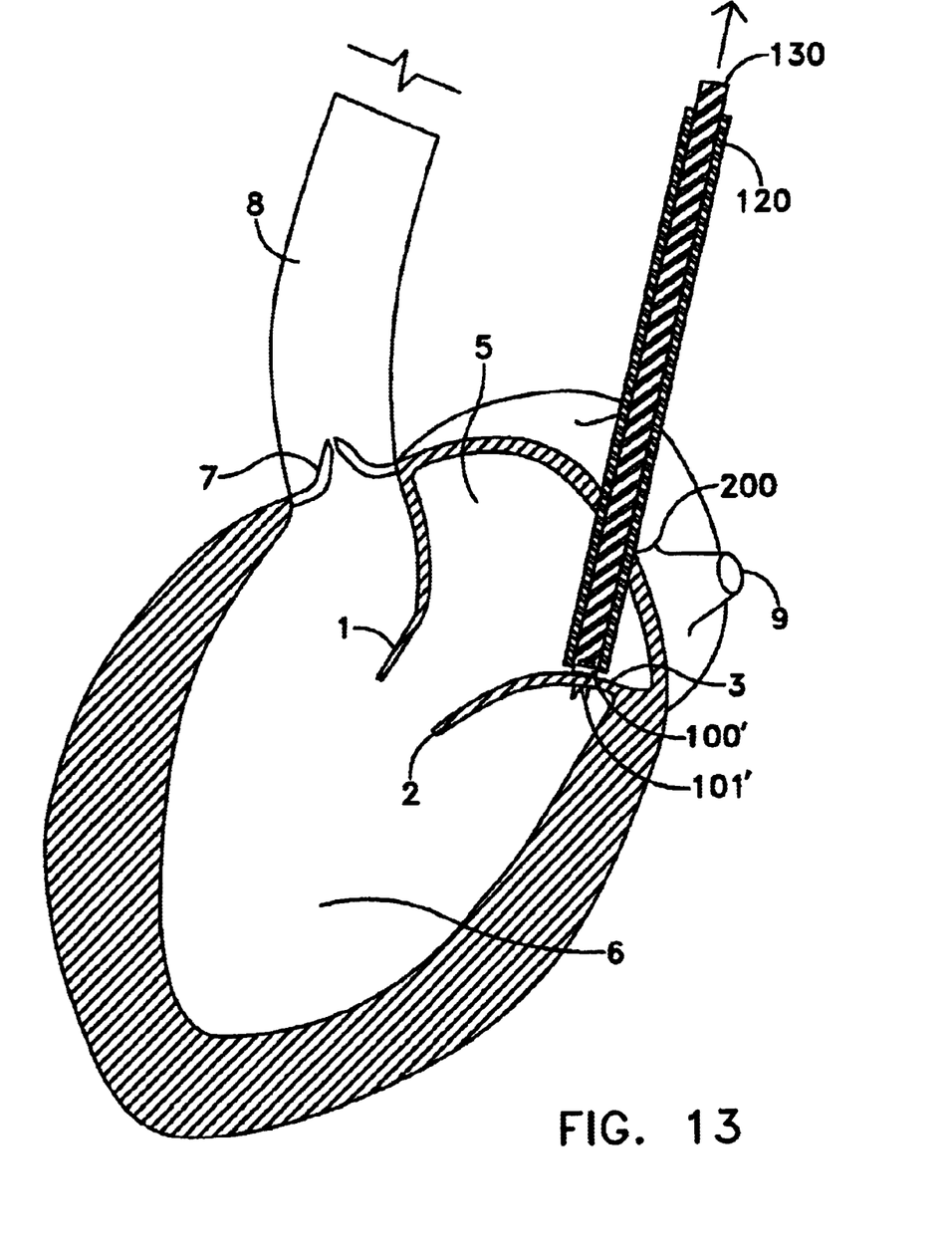
FIG. 13 is a schematic sectional view showing the application of a single plication band to the posterior annulus of the mitral valve.

FIG. 13 depicts an exemplary method of placement of a plication band into the mitral annulus. A deployment instrument, for example, the aforementioned deployment instrument consisting of pull rod 130 and outer pusher cannula 120, has been inserted through a small atriotomy 200 into left atrium 5. Plication band 100' has been advanced against the posterior portion of mitral annulus 3 and the two ends 101' of plication band 100' have pierced the tissue of annulus 3. More particularly, the deployment instrument has contracted plication band 100' by retracting central pull rod 130 relative to outer pusher cannula 120 in the manner previously described, causing mitral annulus 3 to decrease in circumference.

This figure illustrates neighboring cardiac anatomy to provide a frame of reference. Aorta 8 is illustrated, with aortic valve 7 depicted in its closed position during diastole. Anterior leaflet 1 and posterior leaflet 2 of the mitral valve is shown extending into left ventricle 6. Pulmonary vein 9 is shown entering left atrium 5.

Left atrial access has the advantage of providing a relatively straight insertion path for the plication bands of the present invention. The mitral annulus is readily accessible through the left atrium, allowing a relatively straight deployment instrument to access all areas of the posterior mitral annulus. Blood pressure within the left atrium is also relatively low, minimizing the risks of uncontrollable bleeding through the atriotomy during an off-pump procedure. Bleeding may be controlled by placing a pursestring suture around the atriotomy, or by forming a well at the access site filled with saline, or through the use of an expanding access cannula that applies pressure to the insertion site. Other methods are known in the art and do not serve to limit the scope of the present invention.

The devices of the present invention may alternatively be inserted through any one of a variety of other approaches that may be advantageous in particular patient populations. The plication band(s) may be inserted into the arterial system remote from the mitral valve and then advanced into the left ventricle or left atrium at the distal end of an elongated tubular deployment system. The plication band(s) may also be deployed directly through the left ventricle. The plication band(s) may, alternatively, be delivered into the venous system or directly into the right side of the heart. The plication bands can then be advanced through the atrial or ventricular septum to the site of implantation. They may be inserted into the mitral annular tissue from the atrial side or from the ventricular side.

Further, the devices of the present invention may alternatively be inserted into the arterial or venous system remote from the mitral valve and then advanced into the cardiac veins or arteries at the distal end of an elongated system. The plication bands may then be deployed directly through the cardiac venous or arterial wall, in proximity to the mitral annulus, so as to effect a desired geometric change in the mitral annulus.

Further, the devices of the present invention may alternatively be inserted into the area outside of the heart, in proximity to the mitral annulus, at the distal end of an elongated tubular deployment system. The plication bands may then be deployed directly into or through the cardiac wall, into tissue in proximity to the mitral annulus, so as to effect a desired geometric change in the mitral annulus.

The devices and methods of the present invention may further be applied to any or all of the cardiac valves.

The linkage constructs depicted in FIGS. 4–6, 14–19 and 22–24 may be secured to each plication band or to fewer than the total number of plication bands used in a procedure.

The plication bands shown in FIGS. 1–24 should be viewed as exemplary embodiments only and are not intended to restrict the scope of the present invention. Many other embodiments will be apparent to those skilled in the art in view of the present disclosure.

Figure 25:
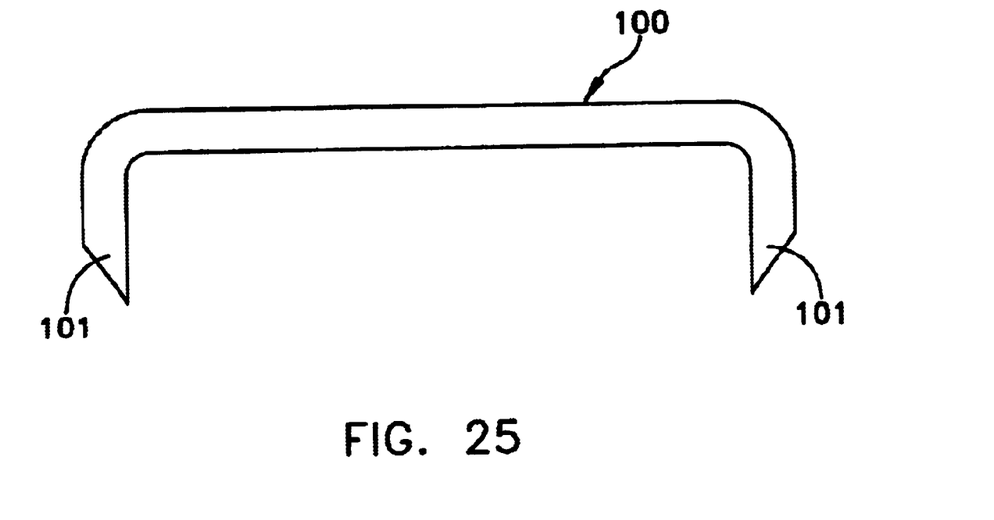
FIGS. 25 and 26 illustrate an alternative form of plication band formed in accordance with the present invention.
Figure 26:
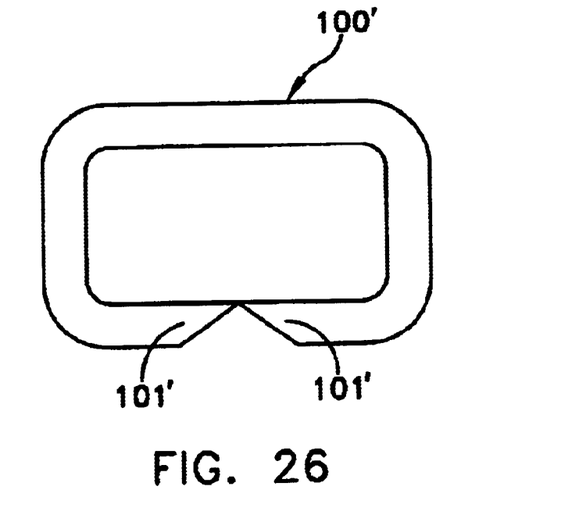

Thus, for example, in FIGS. 25 and 26, there is shown a plication band 100 which is generally similar to the plication band 100 shown in FIGS. 7–12, except that its sharpened ends 101' directly oppose one another after constriction of the device (FIG. 26).

Figure 27:
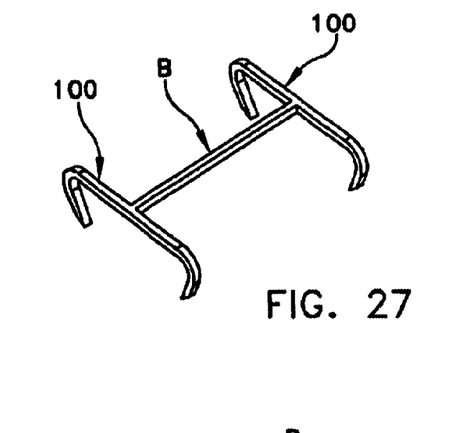
FIGS. 27, 27A, 27B, 28 and 29 illustrate other annulus-constricting constructs, and deployment tool, formed in accordance with the present invention.
Figure 28:
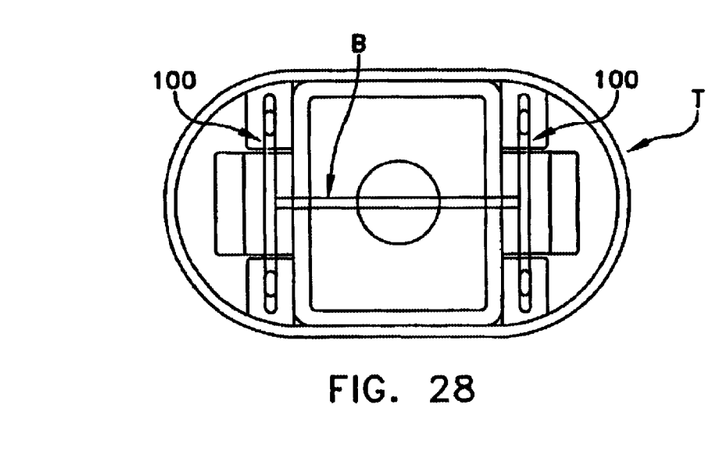
Figure 29:
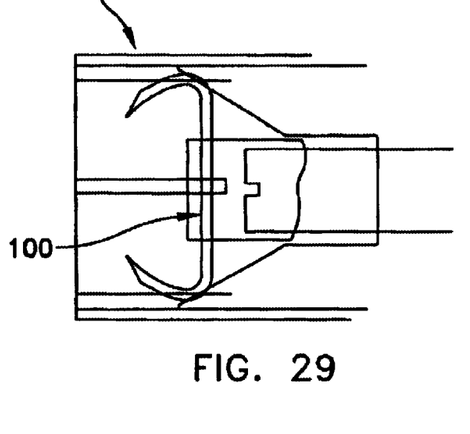

Similarly, in FIGS. 27–29, there is shown a construct which comprises a pair of plication bands 100 integrally joined to one another by a bridge B. Here, the construct is set as a single unit, e.g., by the tool T shown in FIGS. 28 and 29, and the bridge B may thereafter be further manipulated after setting so as to draw the annulus tissue closer together.

In this embodiment, the plication bands 100 are shown perpendicular to bridge B, thus resulting in plication of the annular tissue in two directions. Alternatively, plication bands 100 may be replaced by some other form of fixation (e.g., barbs, sutures, or glues) that may or may not itself provide annular plication, since bridge B may be considered the primary form of annular plication.

Figure 27A:
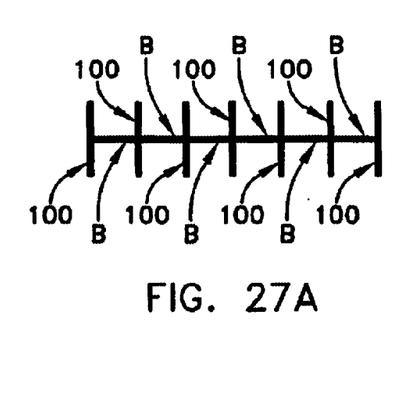

Additionally, a plurality of the constructs shown in FIG. 27 may be combined together into a single construct such as that shown in FIG. 27A. In essence, a plurality of the constructs shown in FIG. 27 are linked together so as to form the one long chain shown in FIG. 27A. Tool T would fixate the first two placating bands 100 into the annular tissue. Subsequently, tool T would bend the first bridge B to plicate the tissue between the first two placating bands. Subsequently, until a sufficient amount of annular tissue has been plicated, tool T would advance to the next plication band linked by another bridge B. Tool T would fixate that next plication band 100 into the adjacent annular tissue and subsequently bend the second linked bridge B so as to plicate the tissue between the current and previous plication band 100. Again, with this construction, plication bands 100 may be replaced with some other form of fixation (e.g., barbs, sutures or glues) if only the bridges B are to be used for plication.

Figure 27B:
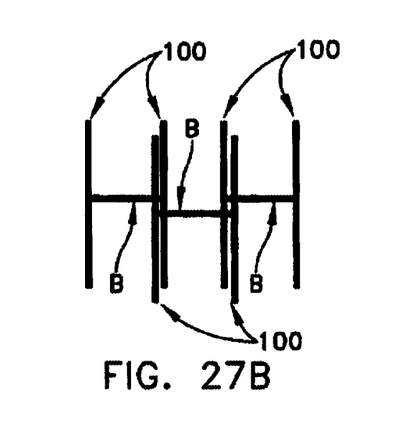

An alternative to the aforementioned chain device of FIG. 27A is a method to create a long chain of linked bridge B's by overlapping the individual plicating devices depicted in FIG. 27. Looking now at FIG. 27B, a single plicating device of the type shown in FIG. 27 would be placed and plicated by tool T. Another placating device would then be placed such that one of it's plication bands 100 would overlap the placting band and/or bridge B of the previously-placed plicating device thereby forming a partially linked structure. This procedure may be repeated as many times as desired so as to create a linked structure of the appropriate length.

Figure 30:
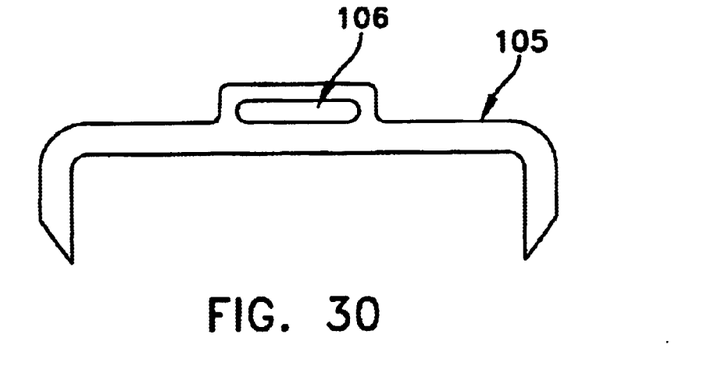
FIGS. 30–32 illustrate yet another form of plication band formed in accordance with the present invention.
Figure 31:
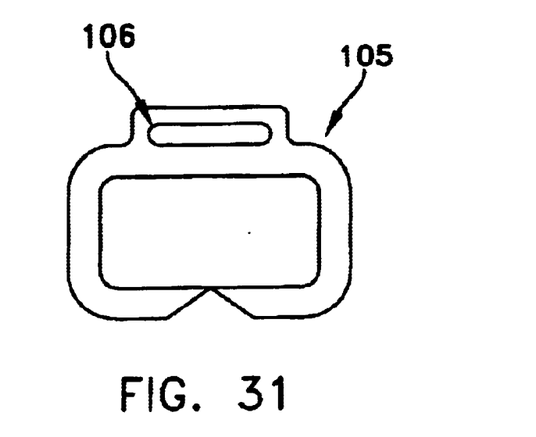
Figure 32:
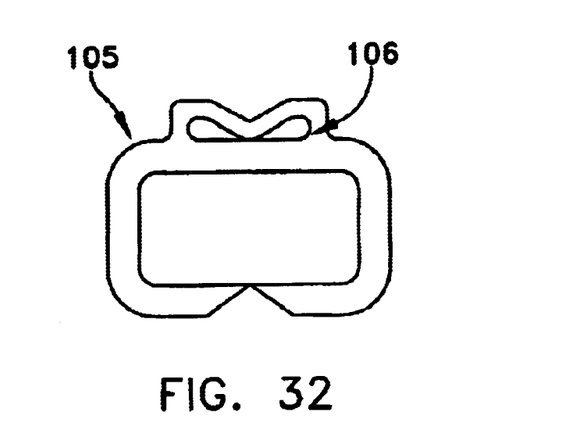

Furthermore, in FIGS. 30–32, there is shown a plication band 105 which is generally similar to the plication band 105 shown in FIGS. 20–24, except the through-hole 106 is elongated so as to accommodate a flattened band or strap rather than a round suture as shown in FIGS. 20–24.

Figure 33:
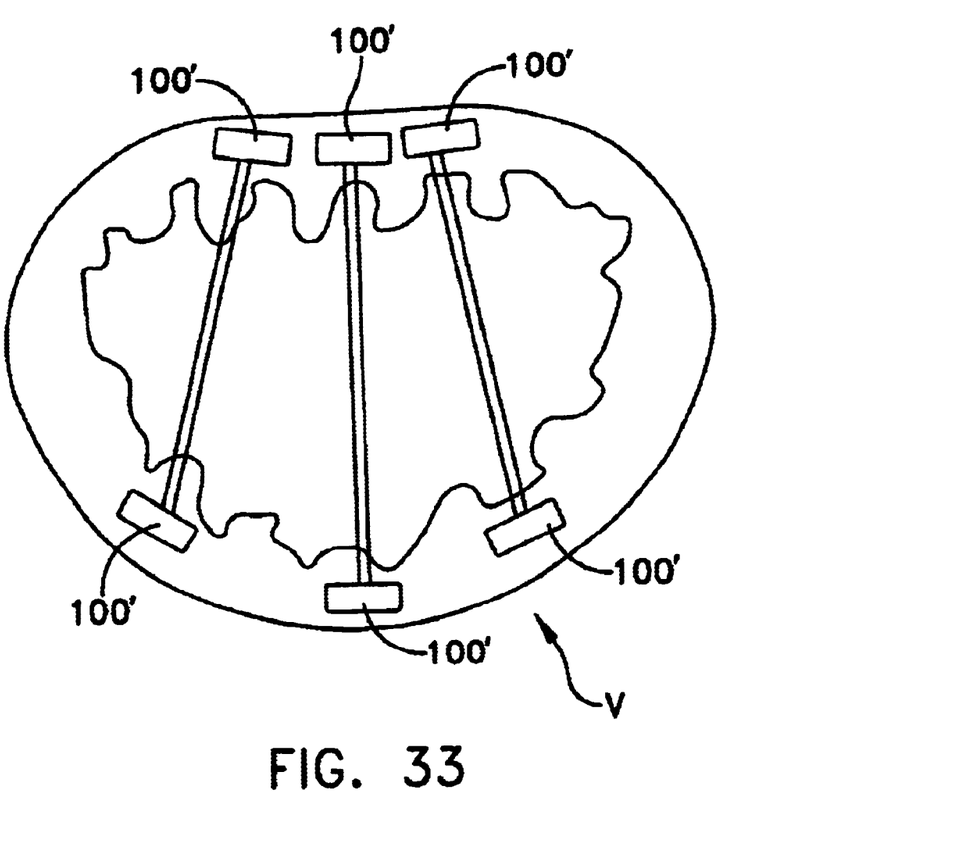
FIG. 33 is a schematic view illustrating a mitral valve repair in accordance with the present invention.

If desired, and looking now at FIG. 33, one or more pairs of plication bands 100', each pair being connected by a linkage strip 300, may be stretched from the posterior annulus to the anterior annulus, whereby to draw the two portions together and thereby reduce or eliminate mitral regurgitation. In addition, the linkage strips 300 may also act as stops to physically limit mitral leaflet prolapse and thereby improve valve function. Where linkage strips 300 cross the mouth of the mitral valve, it may be desirable to form the linkage strips fairly narrow, e.g., in the form of thin strips or filaments.

Still other embodiments will be apparent to those skilled in the art in view of the present disclosure.

What is claimed is:

1. Apparatus for effecting a desired geometric change in the annulus of a heart valve and limiting mitral leaflet prolapse, said apparatus comprising:

first and second plication bands, each said plication band comprising:

first and second substantially straight and parallel legs, each having a first end, the first ends of said first and second legs being adapted to pierce heart valve tissue; and a bridge having first and second ends, the first end of said bridge being connected to said first leg and the second end of said bridge being connected to said second leg, such that the first ends of said first and second legs are separated by a first distance;

said bridge being configured such that when the first ends of said first and second legs have pierced tissue at the first distance, said bridge is deformable so as to cause the first ends of said first and second legs to each move toward the other so as to thereafter be opposed to each other first end-to-first end with a distance of less than the first distance therebetween, whereby said first and second legs gather together pierced tissue to effect a contraction of the annulus of the heart valve; and an elongated linking strip having first and second ends and connected proximate the first end thereof to said first plication band and proximate the second end thereof to said second plication band, the linking strip being adapted to extend across the annulus of the heart valve and to draw the first and second plication bands toward each other.

2. A method for effecting a desired geometric change in the annulus of a heart valve and limiting mitral leaflet prolapse, said method comprising the steps of:

providing apparatus for effecting a contraction in the annulus of the heart valve, the apparatus comprising:

first and second plication bands, each plication band comprising:

first and second substantially straight and parallel legs, each having a first end, the first ends of said first and second legs being adapted to pierce heart valve tissue; and a bridge having first and second ends, the first end of said bridge being connected to said first leg and the second end of said bridge being connected to said second leg, such that the first ends of said first and second legs are separated by a first distance;

said bridge being configured such that when the first ends of said first and second legs have pierced tissue at the first distance, said bridge is deformable so as to cause the first ends of said first and second legs each to move toward one another so as to thereafter be separated by a second, shorter distance, whereby said first and second legs gather together pierced tissue to effect the contraction in the annulus of the heart valve; and a linking construct connected proximate a first end thereof to said first plication band and proximate a second end thereof to said second plication band;

deploying the first plication band in a first portion of tissue; and deploying the second plication band in a second portion of tissue such that the linking construct extends across a mouth of the valve and draws the first and second portions of tissue together, thereby limiting leaflet prolapse.

\* \* \* \* \*